United States Patent
Vanderzee et al.

(10) Patent No.: US 8,498,885 B2
(45) Date of Patent: Jul. 30, 2013

(54) PREDICTING PROVIDER NEGOTIATED RATES

(75) Inventors: Matthew Vanderzee, San Francisco, CA (US); Anshul Amar, San Francisco, CA (US); Jim Griswold, San Francisco, CA (US); John Zedlewski, San Francisco, CA (US); Naveen Saxena, San Francisco, CA (US); Naomi Allen, San Francisco, CA (US)

(73) Assignee: Castlight Health Inc., San Francisco, CA (US)

( * ) Notice: Subject to any disclaimer, the term of this patent is extended or adjusted under 35 U.S.C. 154(b) by 0 days.

(21) Appl. No.: 13/191,718

(22) Filed: Jul. 27, 2011

(65) Prior Publication Data

US 2012/0259662 A1 Oct. 11, 2012

Related U.S. Application Data

(60) Provisional application No. 61/472,588, filed on Apr. 6, 2011.

(51) Int. Cl.
*G06Q 40/00* (2012.01)

(52) U.S. Cl.
USPC .................................. 705/4; 705/35

(58) Field of Classification Search
USPC ........................................ 705/4, 35
See application file for complete search history.

(56) References Cited

U.S. PATENT DOCUMENTS

| | | | |
|---|---|---|---|
| 6,957,218 B1 | 10/2005 | Wyatt | |
| 7,406,427 B1* | 7/2008 | Guyan et al. | 705/4 |
| 7,720,697 B1 | 5/2010 | Silverstein | |
| 2003/0216946 A1* | 11/2003 | Ferraro | 705/4 |
| 2007/0033070 A1* | 2/2007 | Beck et al. | 705/2 |
| 2007/0192144 A1* | 8/2007 | Hauer et al. | 705/3 |
| 2009/0157435 A1 | 6/2009 | Seib | |
| 2010/0070409 A1 | 3/2010 | Harrison et al. | |
| 2010/0116882 A9 | 5/2010 | Harrison et al. | |
| 2011/0071854 A1* | 3/2011 | Medeiros et al. | 705/4 |
| 2012/0054119 A1* | 3/2012 | Zecchini | 705/347 |

* cited by examiner

*Primary Examiner* — William Rankins
(74) *Attorney, Agent, or Firm* — Fenwick & West LLP (57) ABSTRACT

Embodiments of methods and systems for predicting provider negotiated rates are disclosed. One method includes obtaining claims data and provider data, grouping the claims data into priceable units, computing prices for each of the priceable units based on the claims data and the provider data, and estimating provider negotiated rates based on the priceable units and the computed prices for the priceable units.

24 Claims, 11 Drawing Sheets

PREDICTING PROVIDER NEGOTIATED RATES

FIELD OF THE DESCRIBED EMBODIMENTS

The described embodiments relate generally to predicting cost for health care. More specifically, the described embodiments relate to predicting provider negotiated rates which can be used to determine how much a prospective patient can expect to pay out-of-pocket for medical services, including medical procedures, medical provider encounters, hospital visits, prescription drugs, and durable medical equipment.

BACKGROUND

In the world of health care, it is nearly impossible for a patient to know what a given health care service or procedure will cost. This is due to the complex financial and contractual relationships between patients, providers, insurers, and employers. With no visibility into how the pricing works, patients are unable to budget spending, or comparison shop for better prices.

The out of pocket cost a patient is responsible for is based on a number of factors, including: a) the provider's negotiated rate with the patient's insurance company, b) the context in which the procedure occurred (location, other services rendered, etc), and c) attributes of the patient's health plan. The attributes can include the patient's plan provisions, individual and family accumulators such as deductible status, out-of-pocket maximums, and past services used by the patient and family.

When health care providers contract with insurance companies, they agree on a negotiated rate schedule for the procedures the provider offers. These negotiated rates are particularly difficult to determine. These are largely considered confidential, and providers are unwilling to publish them, despite the fact that they have a significant impact on the patient's cost. Since many insurance plans require patients to pay the full negotiated rate before the patient's deductible is met, the negotiated rates are elemental in determining the patient's cost.

Additionally, medical billing revolves around several different procedure coding systems—CPTs, HCPCs, revenue codes, and the like. These arcane coding systems are of minimal relevance to patients, due to their cryptic numeric systems and technical jargon. For a system to help patients understand the costs of medical care, it would need to bridge the gap between the industry's status quo billing procedures, and a patient-oriented view of the medical world.

It is desirable to have a method and/or system for predicting provider negotiated rates which can be used to provide a patient with estimates of how much the patient can expect to pay out-of-pocket for medical services, including medical procedures, medical provider encounters, hospital visits, prescription drugs, and durable medical equipment.

SUMMARY

One embodiment includes a computer-method of predicting provider negotiated rates. The method includes obtaining claims data and provider data, grouping the claims data into priceable units, computing, by a server, prices for each of the priceable units based on the claims data and the provider data, and estimating provider negotiated rates based on the priceable units and the computed prices for the priceable units.

Another embodiment includes a system for predicting provider negotiated rates. The system includes a health care pricing server operative to obtain claims data and provider data from a database. The health care pricing server is operative to group the claims data into priceable units, to compute prices for each of the priceable units based on the claims data and the provider data, to estimate provider negotiated rates based on the priceable units and the computed prices for the priceable units, and to provide the estimated provider negotiated rates through a network to a plurality of user computers.

Another embodiment includes a program storage device readable by a machine, tangibly embodying a program of instructions executable by the machine to perform a method of predicting provider negotiated rates. When executed, an embodiment of the method includes obtaining claims data and provider data, grouping the claims data into priceable units, computing prices for each of the priceable units based on the claims data and the provider data, and estimating provider negotiated rates based on the priceable units and the computed prices for the priceable units.

Other aspects and advantages of the described embodiments will become apparent from the following detailed description, taken in conjunction with the accompanying drawings, illustrating by way of example the principles of the described embodiments.

DETAILED DESCRIPTION OF INVENTION

The described embodiments provide consumer-facing health care pricing method and system that predicts medical care costs for patients. Embodiments of the system include a number of databases, such as: historical claims, provider directory, users, and patient insurance information, and programs, such as, a provider negotiated rate predictor, and a patient out-of-pocket cost calculator. Embodiments of the negotiated rate predictor uses patient claims data to predict negotiated rates for health care providers, by performing the following steps: a) normalize and validate input claims data, b) collect claims into priceable units, c) synthesize priceable units to fill in sparse data, d) compute pricing for priceable units, e) correlate providers who have similar pricing, f) group priceable into bundled services where applicable, and g) export negotiated rates and bundled rates to the patient out-of-pocket cost calculator. The out-of-pocket calculator runs on a hosted server, and is accessed by a plurality of remote users. Using the negotiated rates published by the negotiated rate predictor, it calculates the out-of-pocket cost for medical services, personalized for each user.

As mentioned, the described embodiments provide a health care pricing system to predict patient out of pocket costs for medical care. As mentioned, and as will be further described, for embodiments, this occurs in two components: the provider negotiated rate predictor and the patient out-of-pocket calculator.

Embodiments of the provider negotiated rate predictor include a pricing analytics program that analyzes data (including claim data, provider data, and others) to deduce providers' negotiated rates. The pricing analytics program is operable, for example, on a hosted server or servers, and utilizes a number of databases to store and process the information.

For at least some embodiments, the provider negotiated rate predictor operates in real-time. This can include operating in real-time to support the out of pocket calculator, for example in response to a user search query.

For an embodiment, the negotiated rate predictor imports the raw claim data. Every data source in the health care industry has their own format for representing the data, and so the system must normalize this into a standard format. Each claim is matched to the correct provider in the provider database. Due to the error-prone nature of health care claim data, the system identifies incomplete or erroneous entries, and rejects or repairs them, such that they do not negatively impact the results. Additionally, medical claims are sometimes reversed or adjusted, and so the system must identify these instances and either remove the claim from the system, or alter how the claim is handled. Once the importing is done, the resultant database holds sanitized, normalized, and valid claim data.

The claim data can be incrementally updated on a regular basis, possibly as often as new claims are available. Claims can be imported via any number of formats—CSV, TSC, XML, PDF, Postscript, etc. One example of how this importing process can work is: raw claims are loaded into a raw claim database. The normalization and error correction process takes these raw claims as an input, and outputs normalized claims to the normalized claim database.

For an embodiment, the claims data is parsed. This involves grouping the claims into priceable units. Priceable units are either singleton claims or groups of claims that represent a price that should be propagated into the out of pocket calculator. Because a medical service that a patient receives may be represented by a number of claim line items (CLIs), the system must collect the CLIs that are relevant for a particular service into a priceable unit. A single CLI may end up in multiple priceable units, due to the fact that different medical services may use the same 'building block' billing codes. The notion of a priceable unit helps bridge the chasm between how the health care industry bills for services, and how patients understand the care they get.

An example of a priceable unit includes, for example, an electrocardiogram. This would be a 'singleton priceable unit', as it is typically represented by a single CLI in the data. Another example of a priceable unit is the facility charge for an endoscopy. This charge sometimes is represented by a single CLI, and at other times is billed with multiple CLIs.

Another example of a priceable unit includes a 30-minute office visit. This is also typically a singleton priceable unit.

Embodiments further include synthesis. In certain cases, the data the system has to work with may be sparse—for example, rural geographies, or regions where an insurance company has fewer policy holders. Because of this sparsity of data, the system tries to synthesize priceable units for in-network providers. There are several strategies employed to do so:

A first example of synthesis includes rules-based synthesis. Rules-based synthesis uses health care domain knowledge to fill in priceable units. For example, if a provider does a returning patient office visit, they are likely to also do a first time patient office visit. The system has a series of rules that allows it to effectively create data where there is none.

A second example of synthesis includes probabilistic synthesis. Probabilistic synthesis uses mathematical techniques to operate on the data to make predictions about the services a provider offers. Various Bayesian, clustering, regression, and other strategies are employed to enable this. As an example, the system would look at all the dermatologists in a given state, and compare the data it has for each. By comparing what it sees for these providers, it can then make predictions about their provided procedures.

The results of synthesis can either be stored in the priceable unit database, or synthesis can be computed on demand, with nothing stored in the database.

Embodiments include computing prices for the priceable units. By analyzing the CLIs in a given priceable unit, the system can predict the current price for that priceable unit. Because a provider's rates change over time (typically with an annual rate adjustment), the system looks at the most recent data points to determine the cost. However, if the most recent claim is outdated, the system can try to predict how that rate has changed since the most recent data point it has. In addition, priceable units that were synthesized (and thus have no CLIs) can also be priced through various pricing algorithms.

Various pricing algorithms can be employed to compute prices for priceable units. Based on the type of service and the available data, the system may employ any number of Pricers to find a price. Embodiments include a pricing algorithm that is a technique based on Medicare rates. Since some providers have a certain number of negotiated rates that are based on Medicare fee structures, it is possible to determine these providers' pricing using Medicare rate data. Each provider has a particular multiplier that can be applied to Medicare rates, thus some subset of the provider's procedures can be priced. In other cases, a provider might have several multipliers wherein each multiplier applies to a particular class of services. In other embodiments, the underlying fee structure or "rate sheet" is unknown a priori, but it is deduced through statistical methods including regression or least absolute deviations. Other embodiments utilize pricing algorithms employing such statistical techniques as regression, clustering, Bayesian probability, etc.

Embodiments further include correlating providers that have similar pricing patterns in the claim data. This correlation can follow a similar clustering strategy to probabilistic synthesis, but instead of focusing on the various procedures a provider offers, it determines the providers that charge the same amounts. For example, doctors that are in the same medical practice typically share a contract with a given insurer. This means they tend to have the same billed rates.

There are multiple ways to detect a correlation. Using the provider's practice name or address is often a good indicator. Performing a numerical analysis on claim data can also find providers who bill similarly. Applying multiple strategies for provider correlation also allows the system to measure the strength of a correlation, thus indicating how confident the system is with the connection it has created.

Once correlations are found, the system can share pricing between the correlated providers. This helps fill in pricing, even where there is no original data.

Embodiments include collecting priceable units into bundles. Bundles can be required to represent more complicated episodes of care. For example, many surgeries involve a number of providers—the facility, the surgeon, the anesthesiologist, the pathologist, etc. In addition, a patient encounter with a single provider might result in a bundle of services. To price this service, then, the system combines priceable units from one or many providers to be able to determine the patient's cost.

Various techniques can be used to form these bundles. One way is to employ a two-phase approach. First, the claim data is analyzed to determine what priceable units constitute a valid bundle for the particular type of medical care. Then, the claim data and provider data are analyzed to determine which providers work together. For example, each surgeon may only perform operations at one or a few hospitals. So, the system determines all the valid collections of providers who perform the bundle.

Embodiments further include exporting the pricing data to the patient out-of-pocket calculator. Since the out-of-pocket calculator typically resides on a different server (or multiple servers), it is possible to use various processes to transfer the data. As an example: the pricing data can be sent to a pricing database, which stores multiple versions of the pricing data, for backup purposes. This pricing data is then exported to the server(s) where the out-of-pocket calculator operates, and used to update those programs.

Embodiments of the out-of-pocket calculator component run in real-time on a hosted server that users can access remotely. Users can search for the medical care that they are interested in, or can browse through the catalog of providers and prices. Users can search for procedure by name, or by symptoms, conditions, or treatments. When a user searches for a particular service, the system then returns a list of prices for the providers that offer that medical care. This list of prices can be restricted to the geographical area that the user is searching for, and can further be filtered by provider specialty, location of service, and other parameters. The out-of-pocket calculator can present results in a wide variety of output formats—via a web application (website), a mobile application such as for smart phones and portable devices, a VOIP or IVR application for non-internet usage, thick client applications, etc.

The process this calculator goes through is: a) find all providers in the geographic area of the user that offer the requested service by finding all negotiated rates exported from the negotiated rate predictor, b) for each provider's negotiated rate, apply the attributes of the user's health plan, including benefit accumulator information such as deductible and coinsurance, c) sort the resulting out-of-pocket costs and present to the user. The results can be sorted by price, distance, relevance, provider quality, or other aspects.

Figure 1:
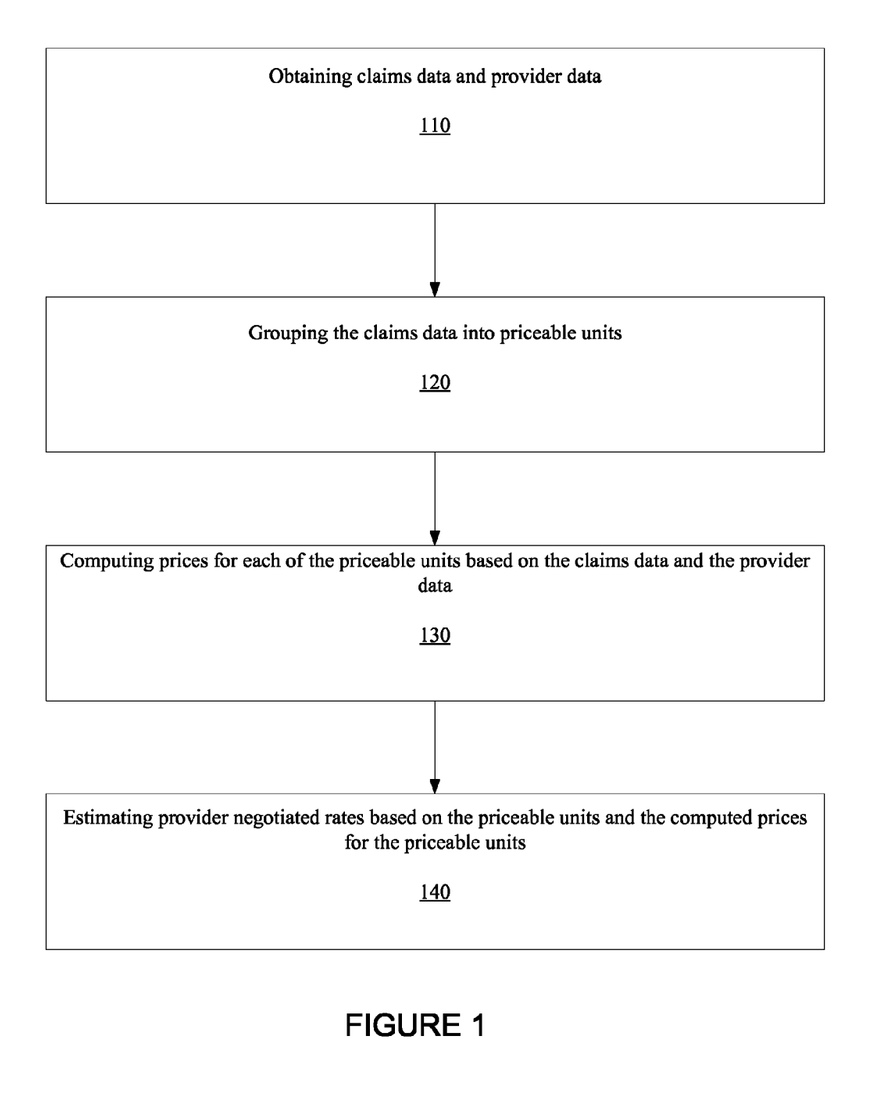
FIG. 1 is a flow chart that includes steps of an example of a method of predicting provider negotiated rates.

FIG. 1 is a flow chart that includes steps of an example of a method of predicting provider negotiated rates. A first step 110 includes obtaining claims data and provider data. The claims data and/or the provider data can be accessed from a database. A second step 120 includes grouping the claims data into priceable units. A third step 130 includes computing, by a server, prices for each of the priceable units based on the claims data and the provider data. A fourth step 140 includes estimating, by a server, provider negotiated rates based on the priceable units and the computed prices for the priceable units. An additional step can include the server providing (displaying or causing to be displayed) the predicted provider negotiated rates to a user or patient. Each of these steps can be completed by one or more networked servers.

An embodiment further includes predicting out-of-pocket expense for a patient by one or more servers. For an embodiment, include collecting one or more priceable units for predicting the out-of-pocket expense of an episode, applying the attributes of the health plan of the patient, and predicting the out-of-pocket expense based on the collected priceable units and the computed prices for the collected priceable units. For another embodiment, this includes collecting one or more priceable units into bundled services for predicting the out-of-pocket expense of an episode, applying the attributes of the health plan of the patient, and predicting the out-of-pocket expense based on the collected priceable units and the computed prices for the collected priceable units. For an embodiment, grouping the priceable units into bundled services includes determining the priceable units within the episode of care in which a cost is being estimated. Again, an additional step can include the server providing (displaying or causing to be displayed) the out-of-pocket expense to a user or patient.

Priceable units are collected into bundles according to the requirements of the medical care being priced. Embodiments of the bundles include predefined templates. For example, a colonoscopy typically has a practitioner component and a facility component. Other bundles may have optional components, or may change based on the provider of the service. Bundles can also be user defined. That is, for embodiments, the system allows the user to choose their configuration, and then the bundle is built based on the user's selections.

An embodiment further includes synthesizing additional priceable units. For one implementation, the additional priceable units are synthesized to fill an array, wherein a size of the array is selectable. It is to be understood that new priceable units can be stored in any type of object. An array is a specific implementation of an object. The array can be visualized as having every provider on one axis, and every procedure on the other axis. That is, the size of the array is dependent upon the number of providers and the number of procedures. This creates an array of possible procedures that each provider can perform.

For another implementation, the additional priceable units are synthesized in real-time as required to predict at least one of the provider negotiated rate or an out-of-pocket expense. For an embodiment, synthesizing additional priceable units includes creating data based on health care knowledge. For an embodiment, the additional priceable units are synthesized in real-time as required to predict at least one of the provider negotiated rate or an out-of-pocket expense.

Various methods can be used for computing the prices. For an embodiment, computing prices includes correlating providers having similarities. The similarities can include similar pricing schedules or similar geographies of the providers.

As previously described, claims data is obtained. For an embodiment, obtaining the claims data can includes normalizing data into a standard format, identifying and rejecting incomplete or erroneous data, and/or identifying instances of reversed or adjusted data. The result is the generation of a database that contains sanitized, normalized valid claim data.

Further, provider data is obtained. For an embodiment, obtaining the provider data includes at least one of normalizing data into a standard format, identifying and rejecting incomplete or erroneous data, identifying instances of reversed or adjusted data, thereby generating a database that contains sanitized, normalized valid claim data.

For at least some embodiments, normalizing the data involves a number of steps. One primary step is to remove insurer- or employer-specific fields. Since the provider of the data often builds their own data format, there are often individual encodings or other nuances to the data. These are removed during the normalization process.

Incomplete or erroneous data is identified through a number of different methods. Some of the more straightforward methods are by nature required—for example, a CLI must have a provider, since some provider filed the claim. If that data field is missing, it indicates there is an issue with that record. Another way of detecting bad data is having expected ranges for each field. For example, if a charge amount for a claim was one billion dollars, this would be outside the expected range, and therefore indicates some issue with the data.

As previously described, embodiments include grouping the data. That is, the claims data is parsed. For an embodiment, this includes collecting claim line items (CLI) of entered claims—that are relevant to a particular priceable unit. It should be noted that a single CLI may be relevant to multiple priceable units.

For an embodiment, computing prices for the priceable units includes for each priceable unit, analyzing claim line items (CLI) of the priceable unit. For another embodiment, computing prices for the priceable units includes for each priceable unit, applying various techniques on claim line item (CLI) data to determine the price, including at least one of linear regression, logistic regression, Bayesian inference, neural networks, statistical processes, or mathematical processes. For another embodiment, computing prices for the priceable units includes importing medicare rates or other publicly available rate sheets, computing each provider's multiplier of an underlying rate sheet, and computing prices for each provider's priceable units. For another embodiment, computing prices for the priceable units includes deducing an underlying rate sheet from multiple providers' claim line item (CLI) using mathematical methods, computing each provider's multiplier of the underlying rate sheet, and computing prices for each provider's priceable units based on the provider's multiplier.

As previously described, embodiments include synthesizing additional priceable units. This can include synthesizing priceable units for in-network providers. As previously described, this can include Rule-based synthesis in which data is created where there is none based on, for example, general health care knowledge. This can also include Probabilistic synthesis in which data is predictive based on existing knowledge of similar providers. That is, for example, similar providers typically have similar costs.

Figure 2:
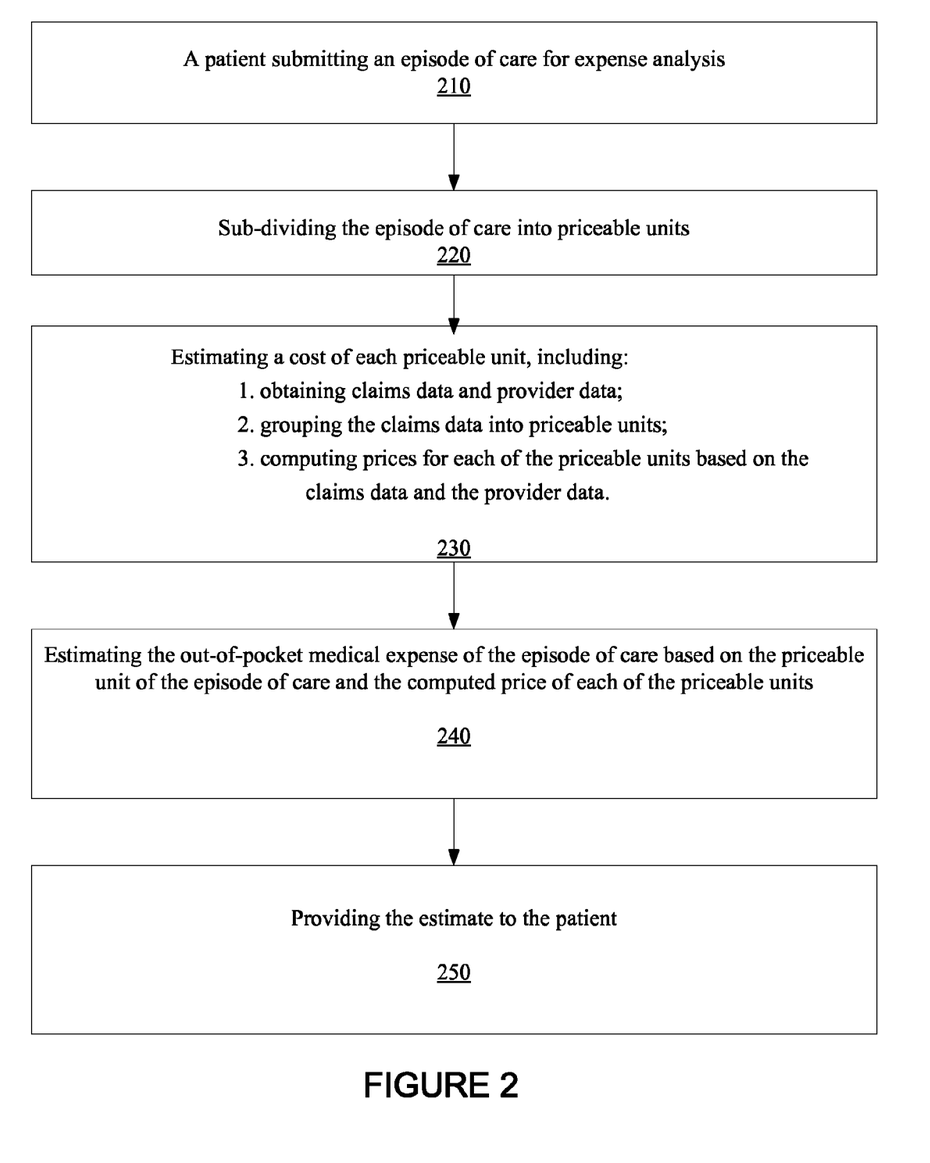
FIG. 2 is a flow chart that includes steps of an example of a method of calculating an out-of-pocket medical expense.

FIG. 2 is a flow chart that includes steps of an example of a method of calculating an out-of-pocket medical expense. A first step 210 includes a patient submitting an episode of care for expense analysis. A second step 220 includes sub-dividing the episode of care into priceable units. A third step 230 includes estimating a cost of each priceable unit. For an embodiment, the third step 230 includes at least one of obtaining claims data and provider data, grouping the claims data into priceable units, and computing prices for each of the priceable units based on the claims data and the provider data. A fourth step 240 includes estimating the out-of-pocket medical expense of the episode of care based on the priceable unit of the episode of care and the computed price of each of the priceable units. A fifth step 250 includes providing the estimate to the patient.

Figure 3:
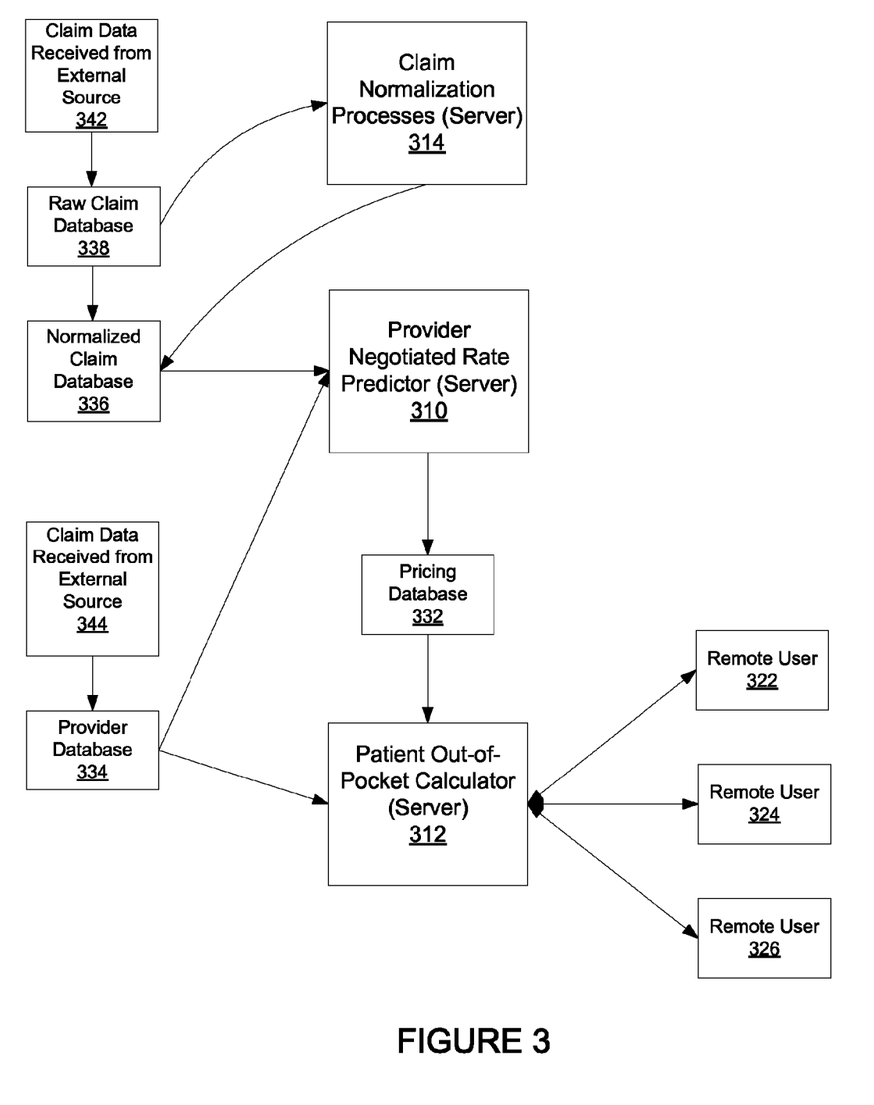
FIG. 3 shows an example of a network of servers, data bases and user, according to the described embodiments.

FIG. 3 shows an example of a network of servers, data bases and user, according to the described embodiments. A first server 310 includes the provider negotiated rate predictor analysis which can include, for example, at least a portion of the method shown in FIG. 1. A second server 320 includes the patient out-of-pocket calculator which can include, for example, at least a portion of the method shown in FIG. 2.

As shown, the first server 310 (provider negotiated rate predictor or health care pricing server) receives normalized claims information from a normalized claim database 336. Claims data can be received from external sources (342) and stored in a raw claim database 338. As shown, a server 314 (which can be included within the health care server) can convert the raw claims data of the raw claim database 338 into normalized claims data which is stored in the normalized claim database 336. The first server 310 can additionally receive provider data from a provider database 334. For embodiments, the provider database 334 receives provider data from external sources (344). The first server 310 can store estimated pricing in a pricing database 332. The estimated pricing can include the estimated price of a priceable unit. While the server 314 and the first server 310 are shown as separate servers, it is to be understood that these may exist as a single server, or the functionality of the servers 310, 314 may be spread over additional servers.

As shown, second server 320 (patient out-of-pocket calculator) can receive, for example, expense analysis requests from users (patients) 322, 324, 326 for episodes of care. Based on the provider information of the provider database 334 and the pricing information of the pricing database 332, the second server can estimate the out-of-pocket costs of the expense requests of the users (patients) and provide the estimated out-of-pocket costs to the users 322, 324, 326.

It is to be understood the each of the servers 310, 312, 314 can include any number of networked servers, or alternatively, can all be included within a single server. Additionally, the databases 332, 334, 336, 338 can be located wherever convenient. The users 322, 324, 326 can include user computers that are coupled through a network to the second server 312.

Figure 4:
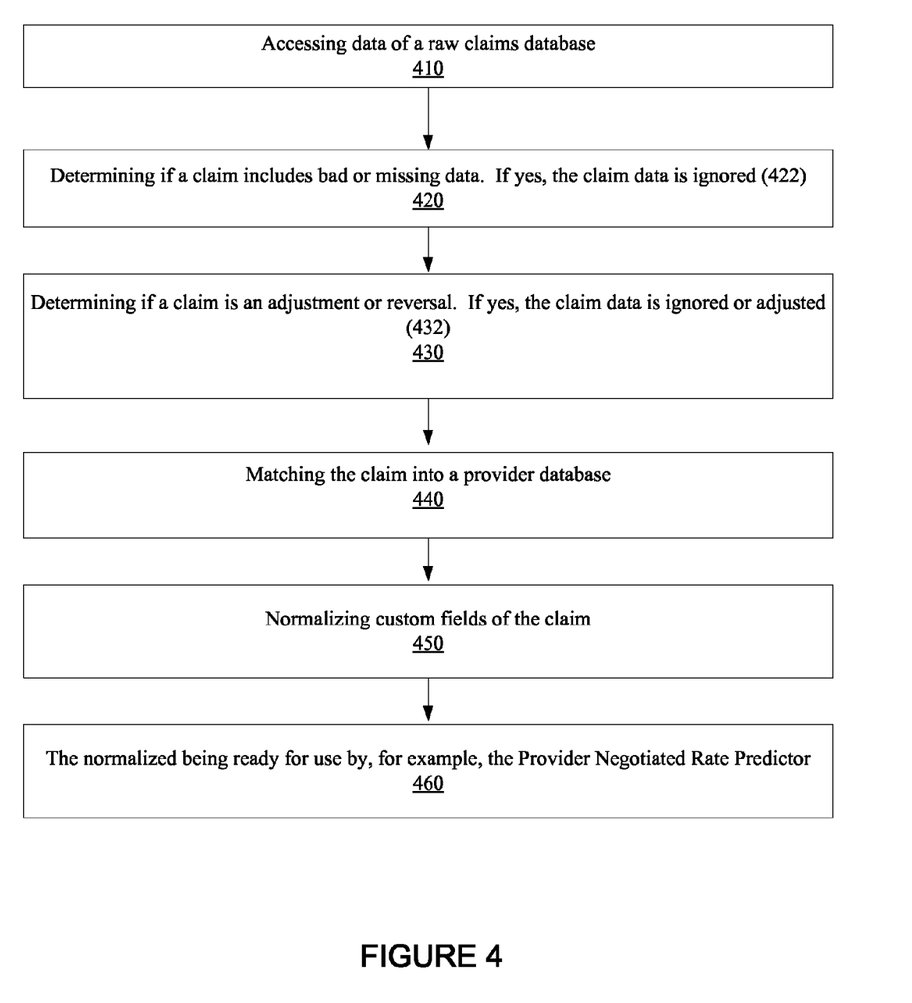
FIG. 4 is a flow chart that includes the steps of an example of a method of importing claims data.

FIG. 4 is a flow chart that includes the steps of an example of a method of importing claims data. The steps of FIG. 4 could be operable, for example, by the server 314 of FIG. 3. A first step 410 includes accessing data of a raw claims database. A second step 420 includes determining if a claim includes bad or missing data. If yes, the claim data is ignored (422). A third step 430 includes determining if a claim is an adjustment or reversal. If yes, the claim data is ignored or adjusted (432). A fourth step 440 includes matching the claim into a provider database. A fifth step 450 includes normalizing custom fields of the claim. A sixth step 460 includes the normalized claim being ready for use by, for example, the provider negotiated rate predictor.

Figure 5:
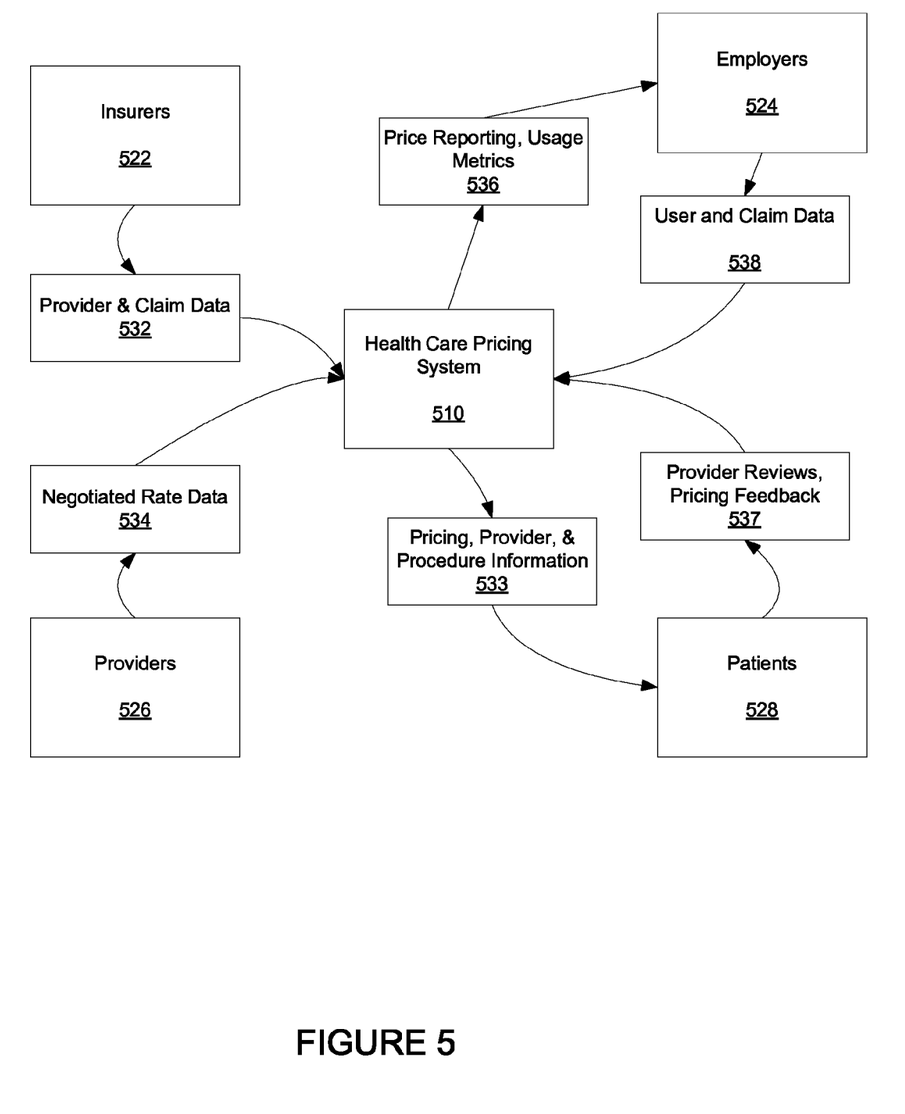
FIG. 5 generally provides a relationship between different parties of a health care system that can utilize the described embodiments.

FIG. 5 generally provides a relationship between different parties of a health care system that can utilize the described embodiments. As shown, a health care pricing system 510 of the described embodiments is interfaces with insurers 522, employers 524, providers 526 and patients 528.

The health care pricing system 510 uses data acquired from various parties (such as, insurers 522, employers 524, providers 526 and patients 528). Insurers can provide claim data and provider data (532). Employers can provide claim data and user data (538). Providers can provide negotiated rate data and procedure data (534). Employers can access their employee's usage data, as well as financial information about health plan utilization (536). Patients access provider pricing data (533) in the form of out-of-pocket prices, The system also provides users with other information (533) about providers, such as location, quality, and other facts. Patients can also submit provider reviews and pricing feedback (537), which further enhances the system's data.

Figure 6A:
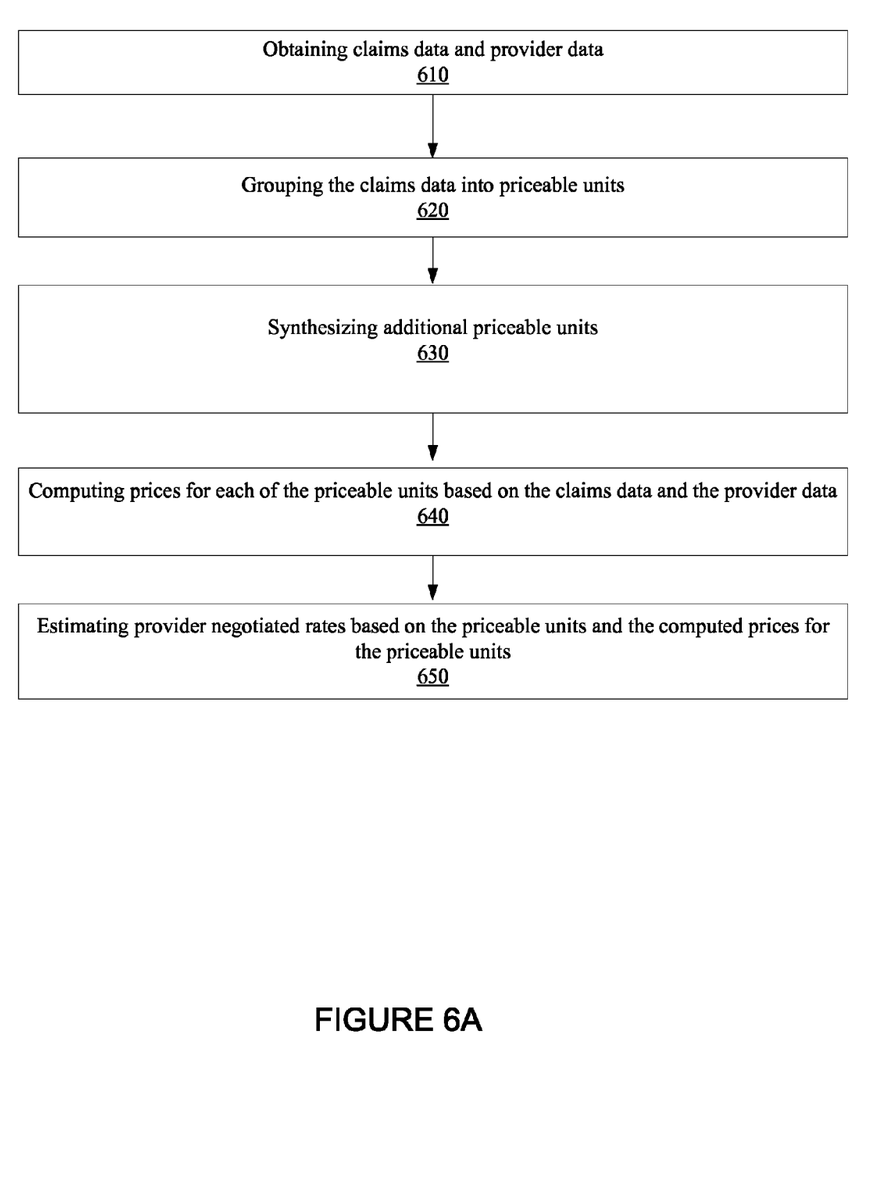
FIG. 6A is a flow chart that includes steps of an example of a method of predicting provider negotiated rates that includes synthesis of additional priceable units.

FIG. 6A is a flow chart that includes steps of an example of a method of predicting provider negotiated rates that includes synthesis of additional priceable units. Embodiments can be used for all types of medical services, including medical procedures, medical provider encounters, hospital visits, prescription drugs, and durable medical equipment. A first step 610 includes obtaining claims data and provider data. A second step 620 includes grouping the claims data into priceable units. A third step 630 includes synthesizing additional priceable units. A fourth step 640 includes computing prices for each of the priceable units based on the claims data and the provider data. A fifth step 650 includes estimating provider negotiated rates based on the priceable units and the computed prices for the priceable units.

As previously described, the additional priceable units can be synthesized to fill an array, wherein a size of the array is selectable. Alternatively, the additional priceable units are synthesized in real-time as required to predict at least one of the provider negotiated rate or an out-of-pocket expense.

Figure 6B:
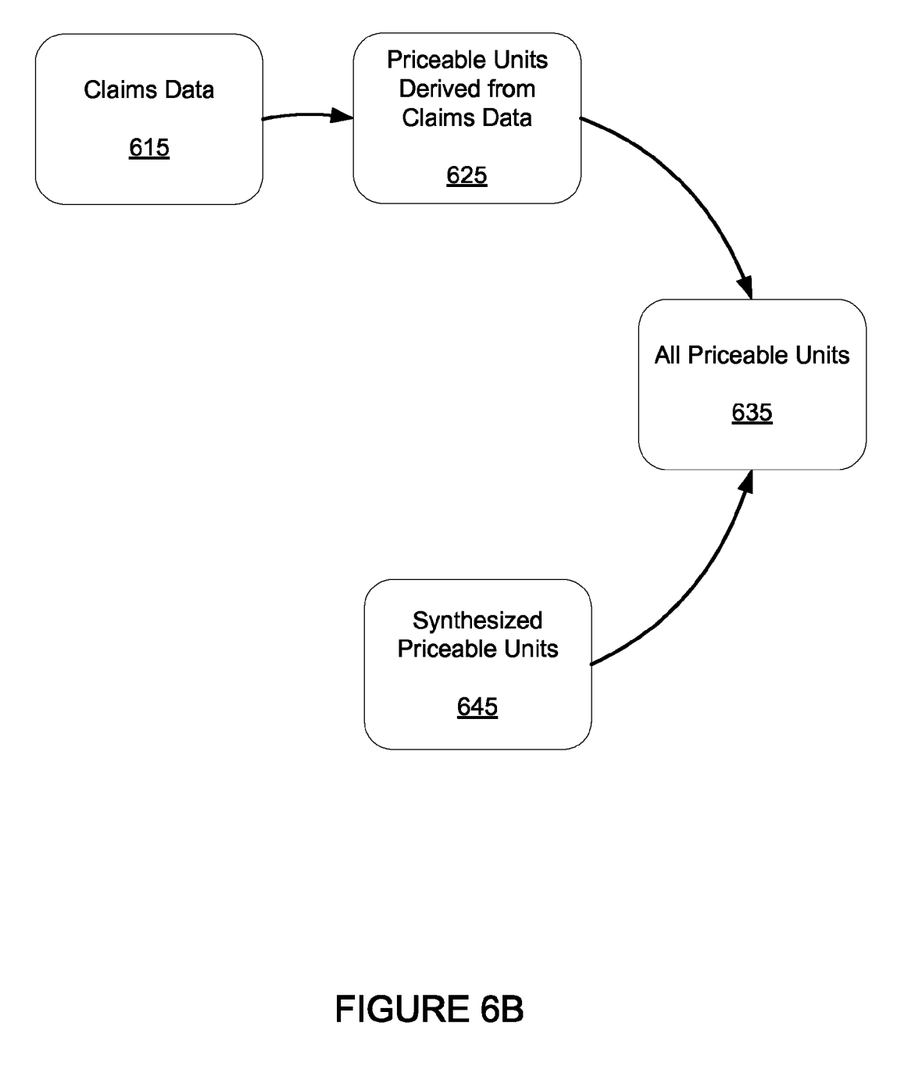
FIG. 6B is a block diagram of a system that the method of FIG. 6A is operable.

FIG. 6B is a block diagram of a system that the method of FIG. 6A is operable. Claims data is obtained (615). Priceable units are then derived from the claims data (625). All pricable units are accumulated (635) from the derived and from synthesized (645) priceable units.

Figure 7A:
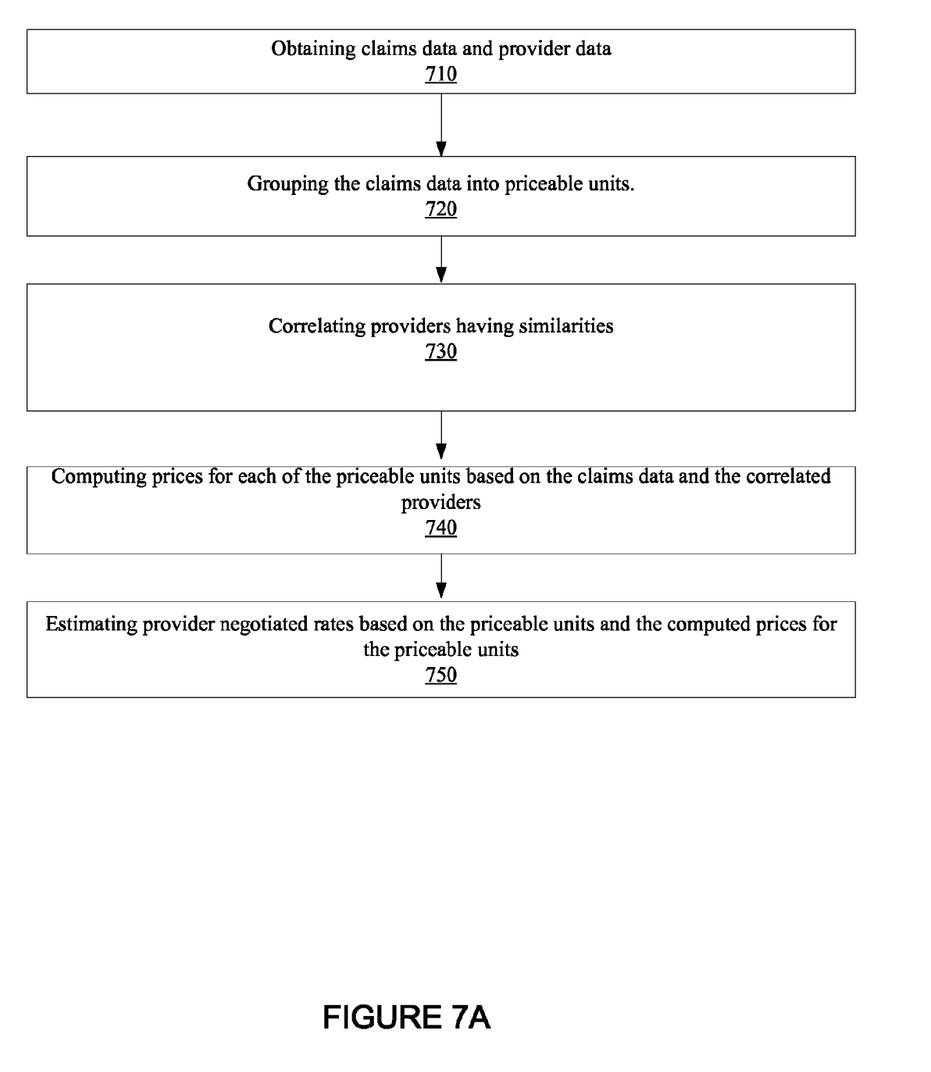
FIG. 7A is a flow chart that includes steps of an example of a method of calculating an out-of-pocket medical expense that includes grouping of claims into priceable units.

FIG. 7A is a flow chart that includes steps of an example of a method of calculating an out-of-pocket medical expense that includes grouping of claims into priceable units. A first step 710 includes obtaining claims data and provider data. A second step 720 includes grouping the claims data into priceable units. A third step 730 includes correlating providers having similarities. A fourth step 740 includes computing prices for each of the priceable units based on the claims data and the correlated providers. A fifth step 750 includes estimating provider negotiated rate based on the priceable units and the computed prices for the priceable units.

Figure 7B:
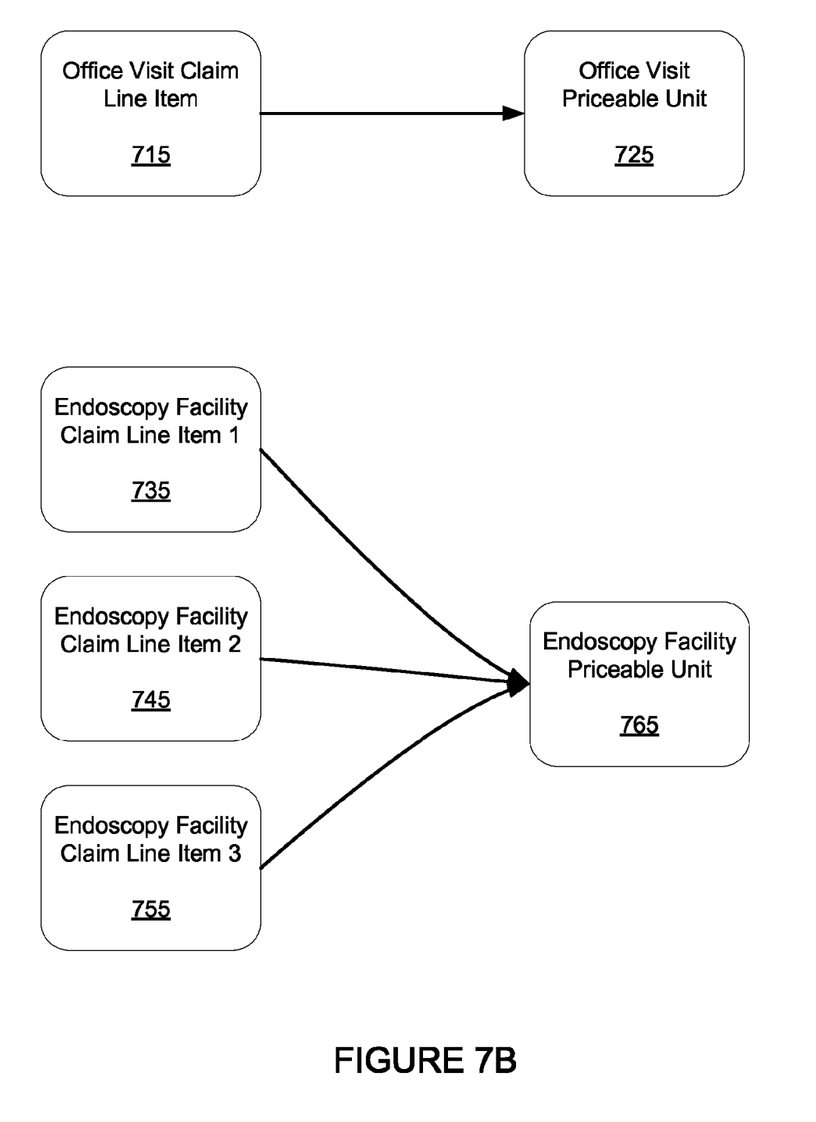
FIG. 7B is a block diagram of a system that the method of FIG. 7A is operable.

FIG. 7B is a block diagram of a system demonstrating several examples of the method of FIG. 7A. An office visit claim line item (715) can be used to determined an office visit priceable unit (725). For an example embodiment, endoscopy facility claim line items 1, 2, 3 (753, 745, 755) are used to determined an endoscope facility priceable unit (765).

Figure 8A:
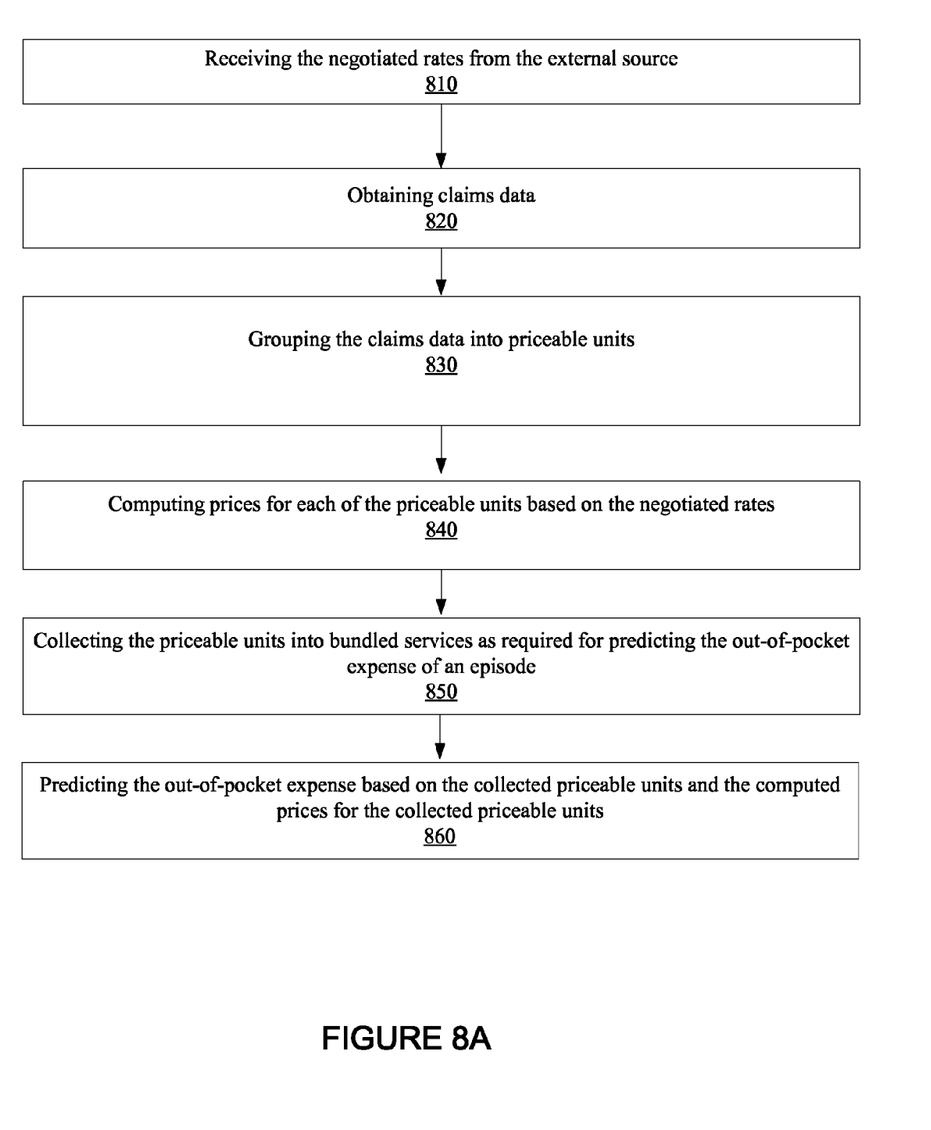
FIG. 8A is a flow chart that includes steps of an example of a method of predicting out-of-pocket expense for a patient that includes receiving the negotiated rates from an external source.

FIG. 8A is a flow chart that includes steps of an example of a method of predicting out-of-pocket expense for a patient the negotiated rates from are received from an external source. A first step 810 includes receiving the negotiated rates from the external source. A second step 820 includes obtaining claims data. A third step 830 includes grouping the claims data into priceable units. A fourth step 840 includes computing prices for each of the priceable units based on the negotiated rates. A fifth step 850 includes collecting the priceable units into bundled services as required for predicting the out-of-pocket expense of an episode. A sixth step 860 includes predicting the out-of-pocket expense based on the collected priceable units and the computed prices for the collected priceable units.

Figure 8B:
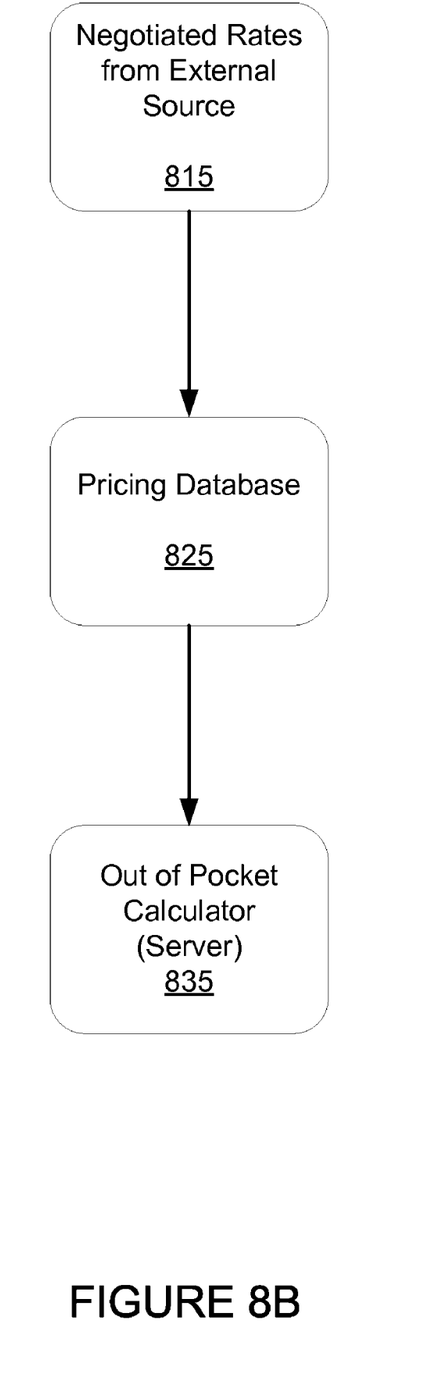
FIG. 8B is a block diagram of a system that the method of FIG. 8A is operable.

FIG. 8B is a block diagram of a system that the method of FIG. 8A is operable. Negotiated rates are received from an external source (815). The negotiated rates are included within a pricing database (825), which can be utilized by the out-of-pocket calculator (835).

As shown and described, at least some of the embodiments described include method or processes that are operable on a machine, such as, a server or computer. Accordingly, at least some embodiments include a program storage device readable by such a machine, tangibly embodying a program of instructions executable by the machine to perform a method of predicting provider negotiated rates. At least one embodiment of the method including obtaining claims data and provider data, grouping the claims data into priceable units, computing prices for each of the priceable units based on the claims data and the provider data, and estimating provider negotiated rates based on the priceable units and the computed prices for the priceable units.

Although specific embodiments have been described and illustrated, the embodiments are not to be limited to the specific forms or arrangements of parts so described and illustrated. The embodiments are limited only by the appended claims.

What is claimed:

1. A computer-method of predicting healthcare provider negotiated rates, comprising:
   obtaining healthcare claims data comprising claim line items for healthcare services and associated with a healthcare provider;
   grouping a plurality of claim line items into priceable units;
   computing, by a server, a price for each of the priceable units by applying at least one of linear regression, logistic regression, Bayesian inference or neural networks to the claim line items; and
   estimating a negotiated rate for the healthcare provider for each of the priceable units based on the computed price for each of the priceable units.

2. The computer-method of claim 1, further comprising predicting an out-of-pocket expense for a patient for a healthcare service, comprising:
   determining one or more priceable units for predicting the out-of-pocket expense of an episode;
   applying attributes of a health plan of the patient; and
   predicting the out-of-pocket expense to the patient for the healthcare service based on the collected priceable units and the computed prices for the collected priceable units.

3. The computer-method of claim 1, further comprising predicting an out-of-pocket expense for a patient for a healthcare service, comprising:
   collecting one or more priceable units into bundled services for predicting the out-of-pocket expense of an episode;
   applying the attributes of the health plan of the patient; and
   predicting the out-of-pocket expense based on the collected priceable units and the computed prices for the collected priceable units.

4. The computer-method of claim 1, further comprising synthesizing additional priceable units.

5. The computer-method of claim 4, wherein additional priceable units are synthesized to fill an array, wherein a size of the array is selectable, and wherein the size of the array is dependent on a number of providers and a number of procedures.

6. The computer-method of claim 4, wherein additional priceable units are synthesized in real-time as required to predict at least one of the provider negotiated rate or an out-of-pocket expense.

7. The computer-method of claim 4, wherein synthesizing additional priceable units comprises creating data based on health care knowledge.

8. The computer-method of claim 4, wherein synthesizing additional priceable units comprises predicting data based on knowledge of similar providers.

9. The computer-method of claim 1, wherein computing prices comprises correlating providers having similarities.

10. The computer-method of claim 9, wherein the similarities comprise at least similar pricing schedules, similar geographies, or shared practices.

11. The computer-method of claim 1, wherein obtaining the claims data comprises at least one of normalizing data into a standard format, identifying and rejecting incomplete or erroneous data, identifying instances of reversed or adjusted data, thereby generating a database that contains sanitized, normalized valid claim data.

12. The computer-method of claim 1, wherein obtaining the provider data comprises at least one of normalizing data into a standard format, identifying and rejecting incomplete or erroneous data, thereby generating a database that contains sanitized, normalized valid provider data.

13. The computer-method of claim 1, wherein grouping the claims data comprises parsing the claims data, and collecting claim line items (CLI) of entered claims that are relevant to a particular priceable unit.

14. The computer-method of claim 1, wherein computing prices for the priceable units comprises:
    importing medicare rates or other publicly available rate sheets;
    computing each provider's multiplier of an underlying rate sheet of the provider; and
    computing prices for each provider's priceable units.

15. The computer-method of claim 1, wherein computing prices for the priceable units comprises:
    deducing an underlying rate sheet from multiple providers' claim line item (CLI) using mathematical methods;
    computing each provider's multiplier of the underlying rate sheet; and
    computing prices for each provider's priceable units based on the provider's multiplier.

16. The computer-method of claim 3, wherein grouping the priceable units into bundled services comprises:
    determining the priceable units within the episode of care in which a cost is being estimated.

17. The computer-method of claim 16, wherein additional priceable units are synthesized to fill an array, wherein a size of the array is selectable.

18. The computer-method of claim 16, wherein additional priceable units are synthesized in real-time as required to predict at least one of the provider negotiated rates or an out-of-pocket expense.

19. A system for predicting provider negotiated rates, comprising:
    a health care pricing server operative to obtain claims data comprising claim line items and associated with a provider from a database;
    the health care pricing server operative to group a plurality of claim line items into priceable units;
    the health care pricing server operative to compute a price for each of the priceable units by applying at least one of linear regression, logistic regression, Bayesian inference or neural networks or statistical processes to the claim line items;
    the health care pricing server operative to estimate a negotiated rate for the provider for each of the priceable units based on the computed price for each of the priceable units;
    the health care pricing server operative to provide the estimated negotiated rate through a network to a plurality of user computers.

20. The system of claim 19, further comprising the health care pricing server operative to predict an out-of-pocket expense for a patient, comprising:
    health care pricing server operative to collect one or more priceable units for predicting the out-of-pocket expense of an episode;
    health care pricing server operative to apply attributes of a health plan of the patient;
    health care pricing server operative to predict the out-of-pocket expense based on the collected priceable units and the computed prices for the collected priceable units.

21. The system of claim 19, further comprising health care pricing server operative to synthesize additional priceable units.

22. The system of claim 19, wherein the health care pricing server operative to compute prices comprises correlating providers having similarities.

23. The system of claim 19, wherein the health care pricing server operative to group the claims data into priceable units comprises parsing the claims data, and collecting claim line items (CLI) of entered claims that are relevant to a particular priceable unit.

24. A non-transitory program storage device readable by a machine, tangibly embodying a program of instructions executable by the machine to perform a method of predicting provider negotiated rates, comprising;
    obtaining claims data comprising claim line items and associated with a provider;
    grouping a plurality of claim line items into priceable units;
    computing a price for each of the priceable units by applying at least one of linear regression, logistic regression, Bayesian inference or neural networks to the claim line items;
    estimating a negotiated rate for the provider for each of the priceable units based on the computed price for each of the priceable units.

* * * * *